United States Patent [19]

Kraus et al.

[11] Patent Number: 5,143,838
[45] Date of Patent: Sep. 1, 1992

[54] METHOD OF PRODUCING THROMBIN FROM FACTOR II USING CALCIUM IONS FOR THE CONVERSION ON AN ANION EXCHANGER

[75] Inventors: Michael Kraus, Frankfurt; Wolfgang Möller, Oberursel, both of Fed. Rep. of Germany

[73] Assignee: Biotest Pharma GmbH, Dreieich, Fed. Rep. of Germany

[21] Appl. No.: 453,555

[22] Filed: Dec. 20, 1989

[30] Foreign Application Priority Data

Dec. 22, 1988 [DE] Fed. Rep. of Germany ....... 3843126

[51] Int. Cl.⁵ .................... C12N 9/74; A61K 35/14; C07K 3/00
[52] U.S. Cl. .................... 435/214; 530/384; 530/395
[58] Field of Search ............... 435/214; 530/384, 395

[56] References Cited

U.S. PATENT DOCUMENTS

| | | | |
|---|---|---|---|
| 4,272,523 | 6/1981 | Kotitschke et al. | 530/384 |
| 4,364,861 | 12/1982 | Mitra et al. | 530/384 |
| 4,380,511 | 4/1983 | Mannuzza et al. | 435/214 |
| 4,391,746 | 7/1983 | Mitra et al. | 530/384 |
| 4,395,396 | 7/1983 | Eibl et al. | 530/384 |
| 4,427,650 | 1/1984 | Stroetmann | 530/384 |
| 4,639,513 | 1/1987 | Hou et al. | 530/395 |
| 4,710,459 | 12/1987 | Bartl et al. | 435/214 |
| 4,780,412 | 10/1988 | Atkinson et al. | 435/219 |
| 4,945,054 | 7/1990 | Fougnot et al. | 435/214 |
| 4,965,203 | 10/1990 | Silbering et al. | 435/214 |

OTHER PUBLICATIONS

Miale, Laboratory Medicine: Hematology, p. 1063, pub. C. V. Mosby Comp., 1972.
Swart et al., Biochim. Biophys. Acta., vol. 222, pp. 692–695, 1970.
Yin et al., Jour. of Biol. Chem., vol. 243, No. 1, pp. 112–117, 1968.
Vician et al., Biochimica et Biophysica Acta., vol. 434, pp. 199–208, 1976.
Becker, "Kinetics of the Bio-Conversion of Prothrombin to Thrombin", article MTI, Mass. pp. 245–262.
Seegers, "Historical Perspective Related to Thrombin", article Wayne State U., Detroit, Mich., pp. 1–9.
120342a: Masaki, "Purification of Prothrombin:", Seikagaku 1968, 40 (12) Chem. Ab. pp. 890–901 (Japan).
English Translation of the Full Reference of "Purification of Prothrombin", Masaki, Seikagaku.

*Primary Examiner*—Douglas W. Robinson
*Assistant Examiner*—Mike Meller
*Attorney, Agent, or Firm*—Sprung Horn Kramer & Woods

[57] ABSTRACT

A method of producing thrombin from Factor II (prothrombin) comprising the steps of:

a) applying a solution of citrated plasma or citrated plasma fraction containing Factor II onto an equilibrated anion exchanger to bind Factor II thereto;

b) applying a solution containing calcium ions to the exchanger to convert the Factor II to thrombin, and c) selectively eluting the thrombin from the carrier.

5 Claims, No Drawings

METHOD OF PRODUCING THROMBIN FROM FACTOR II USING CALCIUM IONS FOR THE CONVERSION ON AN ANION EXCHANGER

The object of the invention is a simple method of isolating a thrombin preparation with a high specific activity and high yield from plasma or plasma fractions containing Factor II.

The plasma protease thrombin is a multifunctional enzyme that can react specifically with proteins and cells. One of the major functions of thrombin in the blood plasma is to convert soluble fibrinogen into insoluble fibrin in the last step of the blood-coagulation cascade. Thrombin can also react with Coagulation Factors V, VII, IX and XIII and with Protein C and activate them. Furthermore, thrombin reacts specifically with platelets and endothelial cells and has the capacity to mitogenetically stimulate fibroblasts. In therapy, thrombin is employed together with fibrinogen and Factor XIII for example in what are called fibrin glues for repairing damaged organs, bones, and vessels. Thrombin is also employed alone to staunch oozing hemorrhages or hemorrhages in the hollow organs.

For all clinical applications whether in therapy or diagnosis, thrombin must be extremely pure in order to avoid undesired side effects, resulting for example from other proteases or coagulation factors. The literature describes several methods of preparing high-purity thrombin, usually with partially purified thrombin or with prothrombin-complex concentrates as the starting material. Most of the work involved in obtaining a high-purity thrombin preparation accordingly consists of obtaining the starting products. The further purification of the thrombin could be performed one or two chromatography steps. The specific activity of the thrombin in the starting material that is subjected to the chromatography has in the past depended on the purity of the Factor II prior to its activation into thrombin and ranged between 20 and 250 NIH units/mg of protein (review in Machovich, R., ed., Thrombin 1 [Boca Raton, 1984], 1-160).

It has up to now been impossible at the state of the art to isolate thrombin in high yield from plasma in a simple and single-step method. At present the standard method of preparing a thrombin concentrate now comprises adsorbing the PPSB Factors II, VII, IX and X from the plasma onto a DEAE-matrix, eluting the Factor II, activating it into thrombin and purifying the thrombin in further steps. The yields of Factor II from the first steps in this method are 40 to 60% of the starting activity in the plasma. Once the Factor II has been activated and further purified into thrombin, the yields will be, depending on the particular method, 20 to 40 NIH units of thrombin per unit of Factor II in the starting plasma and hence approximately 20,000 to 40,000 NIH units of thrombin per liter of plasma.

In the previously known methods of isolating thrombin from plasma it was impossible to avoid previous preparation of the Factor II because activating the factor in the plasma leads to coagulation of the fibrinogen into fibrin, turning the plasma into serum. Aside from the losses of thrombin due to adsorption onto the fibrin, it would become difficult or impossible to further process the serum into other coagulation factors or therapeutically useful plasma proteins. Optimum exploitation of the valuable raw material human blood plasma however demands using only those methods of preparation that will affect the purification of other plasma proteins as little as possible.

The object of the present invention is accordingly to provide a simple method of isolating thrombin from plasma in high yield and with a high specific activity.

This object is realized in accordance with the invention in that the Factor II is adsorbed from the plasma or plasma fractions onto a solid carrier, activated into thrombin on the matrix, and selectively eluted.

It was surprisingly discovered that activating Factor II adsorbed onto the matrix into thrombin yields more and essentially purer thrombin than eluting the factor, activating it into thrombin, and then further purifying it.

The yields obtainable with this method are 70 to 90 NIH units of thrombin per unit of Factor II and hence 70,000 to 90,000 NIH units of thrombin per liter of starting plasma with a specific activity of 800 to 1400 NIH units per mg of protein.

The method in accordance with the invention for isolating thrombin from plasma can be incorporated extremely well into existing fractioning sequences, which usually include a step consisting of adsorbing the PPSB factors from the plasma. The present approach differs from isolating the PPSB factor in the different conditions for elution from the adsorbent.

How a preparation in accordance with the invention can be obtained will now be described.

A solution, preferably human blood plasma or a fraction thereof, that contains Factor II is adsorbed onto a matrix, preferably an anion exchanger or an affinity carrier. The adsorption occurs subject to conditions that are in themselves known and correspond to the state of the art, at low ion strengths of 1 to 15 m S/cm and at a pH of 6.0 to 8.5 with Fraktogel DEAE-TSK (Merck, Darmstadt) for example.

The unbound proteins are washed out with a citrate buffer. The citrate, which would impede activation, is washed out of the matrix with a sodium chloride solution of low ionic strength. For the elution a buffer that contains an activator—$Ca^{2+}$ ions, $Ca^{2+}$ ions plus thromboplastin, or Factor Xa for example—is applied to the matrix. The Factor II is preferably activated into thrombin with $Ca^{2+}$ ions alone by eluting the matrix for 10 minutes to 5 hours with a solution of preferably 20 to 30 mM of $Ca^{2+}$ ions. A particularly high yield of thrombin can be obtained by incubating the column with a solution of $Ca^{2+}$ ions for 10 minutes to 5 hours and subsequent elution.

The fractions with a specific activity of more than 400 NIH units per mg of protein are pooled. The thrombin activity is determined by the conversion of fibrinogen into fibrin (R. L. Lundblad, Biochemistry 10, 13 [1971], 2501-2506) or by the cleavage of a chromogenetic substrate (Chromozym TH, Boehringer). The protein content of the fractions is determined by Bradford's method (M. M. Bradford, Anal. Biochem. 72 [1976], 248-254). The thrombin fraction is concentrated to a level of more than 100 NIH units per ml by methods that are in themselves known, ultrafiltration for example, and filtered sterile. The specific activity is usually approximately 800 to 1400 NIH units per mg of protein.

If greater purity is desired, the specific activity of the thrombin can easily be increased to more than 2000 NIH units per mg of protein by directly adsorbing the thrombin solution eluted from the matrix onto a cation exchanger—SP-Trisacryl (IBF), Fraktogel TSK-Sulfat (Merck), or SP-Sephadex C50 (Pharmacia) for example.

Before or after the thrombin is isolated from the plasma or plasma fractions the batch can be sterilized to inactivate such human-pathogenic viruses as hepatitis non-A/non-B or human immunodeficiency (HIV) by treatment with B-propiolactone and ultraviolet radiation, by treatment with tri-n-butyl phosphate and detergent, or by heating.

The method in accordance with the invention will now be described with reference to the examples.

EXAMPLE 1

A 50-ml column of Fraktogel TSK-DEAE (Merck, Darmstadt) was equilibrated with 10 mM of citrate at a pH of 7.0. 1000 ml of citrated plasma were applied onto the column at a flow rate of 750 ml/hour. The gel was rinsed with 100 ml of 10 mM citrate pH 7.0 and with 100 ml of 75 mM sodium chloride. The thrombin was eluted with 25 mM of $CaCl_2$ at a flow rate of 100 ml/hour for 4 hours. The specific activity of the thrombin eluate was 1000 NIH units per mg of protein. It was possible to obtain 90,500 NIH units of thrombin from 1000 ml of plasma containing 1040 units of Factor II. This is a yield of 87 NIH units of thrombin per unit of Factor II in the starting plasma.

EXAMPLE 2

Each of 1000 ml of citrated plasma at a time were chromatographed over various carriers as described in Example 1. The table shows the results.

TABLE

| Carrier | Specific activity (NIH units of thrombin per mg of protein) | Total yield of thrombin (NIH units) |
| --- | --- | --- |
| DEAE Sephadex A50 | 246 | 85,300 |
| QA-Trisacryl LS | 863 | 63,000 |
| DEAE-Trisacryl LS | 950 | 91,000 |
| Fraktogel TSK-Amino | 1400 | 86,900 |

EXAMPLE 3

1000 ml of cryo-poor plasma was chromatographed over Fraktogel TSK-DEAE (Merck, Darmstadt) as described in Example 1.

The specific activity of the thrombin eluate was 950 NIH units per mg of protein at an overall yield of 72,600 NIH units of thrombin.

EXAMPLE 4

100 ml of the thrombin eluate from Example 1 were immediately applied onto a 15-ml column of the cation exchanger Fraktogel TSK-Sulfat (Merck, Darmstadt), previously equilibrated with 50 mM of sodium chloride.

The gel was washed with 50 ml of 50 mM sodium chloride and with 100 ml of 75 mM phosphate buffer at a pH of 6.5. The thrombin was then eluted with a 250 mM phosphate buffer at a pH of 6.5.

The yield was 86% in relation to the starting eluate and 78,000 NIH units of thrombin out of one liter of starting plasma. It was possible to increase the specific activity of the thrombin to 2400 NIH units per mg of protein.

It will be understood that the specification and examples are illustrative but not limitative of the present invention and that other embodiments within the spirit and scope of the invention will suggest themselves to those skilled in the art.

What is claimed is:

1. A method of producing thrombin from Factor II comprising the steps of:
    a) applying a solution of citrated plasma or citrated plasma fraction containing Factor II onto an equilibrated anion exchanger to bind Factor II thereto;
    b) applying a solution containing calcium ions to the exchanger to convert the Factor II to thrombin, and
    c) selectively eluting the thrombin from the carrier.

2. The method according to claim 1, wherein the anion exchange matrix carries DEAE or QAE groups and is (a) a copolymer of glycidyl methacrylate, pentaerythritol dimethacrylate or polyvinyl alcohol, (b) a copolymer of N-acryloyl-2-amino-2-hydroxymethyl-1,3-propanediol, or (c) a carbohydrate polymer.

3. The method according to claim 1, wherein the anion exchanger has 2-hydroxy-aminopropyl groups.

4. The method according to claim 3, wherein the 2-hydroxy-aminopropyl groups are present on a copolymer of glycidyl methacrylate, pentaerythritol dimethacrylate, and polyvinyl alcohol.

5. The method according to claim 1, wherein the concentration of the calcium ions is 20–30 mM.

* * * * *